(12) United States Patent
Korytko et al.

(10) Patent No.: US 7,988,970 B2
(45) Date of Patent: *Aug. 2, 2011

(54) METHODS OF TREATMENT COMPRISING ADMINISTERING AN ANTI-SCLEROSTIN ANTIBODY

(75) Inventors: Andrew Ihor Korytko, Oceanside, CA (US); David Matthew Marquis, Encinitas, CA (US); Eric Michael Smith, San Diego, CA (US); Barbara Anne Swanson, Encinitas, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/779,438

(22) Filed: May 13, 2010

(65) Prior Publication Data

US 2010/0221263 A1   Sep. 2, 2010

Related U.S. Application Data

(62) Division of application No. 12/160,472, filed as application No. PCT/US2008/056527 on Mar. 11, 2008, now Pat. No. 7,744,874.

(60) Provisional application No. 60/895,813, filed on Mar. 20, 2007.

(51) Int. Cl.
*A61K 39/00* (2006.01)
*A61K 39/395* (2006.01)

(52) U.S. Cl. .............. 424/145.1; 424/130.1; 424/133.1; 424/141.1; 424/142.1

(58) Field of Classification Search .................. None
See application file for complete search history.

(56) References Cited

U.S. PATENT DOCUMENTS

| | | | |
|---|---|---|---|
| 6,395,511 B1 | 5/2002 | Brunkow et al. | |
| 6,489,445 B1 | 12/2002 | Brunkow et al. | |
| 6,495,736 B1 | 12/2002 | Brunkow et al. | |
| 6,803,453 B1 | 10/2004 | Brunkow et al. | |
| 7,192,583 B2 | 3/2007 | Brunkow et al. | |
| 2005/0106683 A1 | 5/2005 | Winkler et al. | |

FOREIGN PATENT DOCUMENTS

| | | |
|---|---|---|
| EP | 1133558 | 8/2006 |
| WO | 0032773 | 6/2000 |
| WO | 0198491 | 12/2001 |
| WO | 03106657 | 12/2003 |
| WO | WO 2004/047609 A2 * | 6/2004 |
| WO | 2005003158 | 1/2005 |
| WO | 2005014650 | 2/2005 |
| WO | 2006119062 | 11/2006 |
| WO | 2006119107 | 11/2006 |
| WO | 2008061013 | 5/2008 |

OTHER PUBLICATIONS

Lewiecki et al. (2009, Expert Opinion Emerging Drug 14:129-144).*
Eddleston et al. (2009, J. Bone Min. Res. 24:1662-1671).*
Li et al. (2009, J. Bone Min. Res. 24:578-588).*
Alves, et al., Rev. Bras. Genet. 4:825-834 (1982).
Balemans, et al, Human Mol. Genetics 10(5):537-543 (2001).
Beighton, et al., Clinical Genetics, 25:175-181 (1984).
Brunkow, et al., Am. J. Hum. Genet. 68:577-589 (2001).
Linear human genomic DNA from chromosome 17, EMBL Accession No. AC003098 (Nov. 14, 1997).
Linear mRNA, human EST, EMBL Accession No. AA393939 (May 19, 1997).
Linear mRNA, human EST, EMBL Accession No. AI113131 (Sep. 4, 1998).
Uitterlinden, et al., Am. J. Hum. Genet. 75:1032-1045 (2004).
Van Hul, et al., Am. J. Hum. Genet. 2:391-399 (1998).
Winkler, et al., The EMBO Journal 22(23):6267-6275 (2003).
Balint, R., et al., "Antibody Engineering by Parsimonious Mutagenesis," Gene 137(1):109-118 (1993).
International Preliminary Report on Patentability issued by the International Bureau of WIPO, Sep. 22, 2009.

* cited by examiner

*Primary Examiner* — Elizabeth C Kemmerer
(74) *Attorney, Agent, or Firm* — Alejandro Martinez; MaryAnn Wiskerchen

(57) ABSTRACT

Humanized and chimeric antibodies are provided that specifically bind human sclerostin and are characterized as having high affinity and strong neutralizing properties. The antibodies of the invention are useful for increasing bone mass, bone mineral density and bone strength and for the treatment of various disorders, e.g., osteoporosis, in human subject.

2 Claims, No Drawings

SEQUENCE LISTING

<160> NUMBER OF SEQ ID NOS: 43

<210> SEQ ID NO 1
<211> LENGTH: 213
<212> TYPE: PRT
<213> ORGANISM: Homo sapiens

<400> SEQUENCE: 1

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

```
Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 2
<211> LENGTH: 444
<212> TYPE: PRT
<213> ORGANISM: Artificial
<220> FEATURE:
<223> OTHER INFORMATION: Miscellaneous construct

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Phe Leu Asn Trp Val Arg Gln Ala Pro Gly Gln Gly Leu Glu Trp Met
        35                  40                  45

Gly Thr Ile Tyr Pro Tyr His Asp Gly Thr Thr Tyr Ser Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Glu Asp Gly Gln Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
```

```
                            340                 345                 350
Gln Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
            435                 440

<210> SEQ ID NO 3
<211> LENGTH: 444
<212> TYPE: PRT
<213> ORGANISM: Artificial
<220> FEATURE:
<223> OTHER INFORMATION: Miscellaneous construct

<400> SEQUENCE: 3

Gln Val Gln Leu Val Gln Ser Gly Ala Glu Val Lys Lys Pro Gly Ala
1               5                   10                  15
Ser Val Lys Val Ser Cys Lys Val Ser Gly Phe Pro Ile Lys Asp Thr
            20                  25                  30
Phe Gln His Trp Val Arg Gln Ala Pro Gly Lys Gly Leu Glu Trp Met
        35                  40                  45
Gly Trp Ser Asp Pro Glu Ile Gly Asp Thr Glu Tyr Ala Ser Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Gly Asp Thr Thr Tyr Lys Phe Asp Phe Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
    210                 215                 220
Pro Pro Cys Pro Ala Pro Glu Phe Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 4
<211> LENGTH: 450
<212> TYPE: PRT
<213> ORGANISM: Artificial
<220> FEATURE:
<223> OTHER INFORMATION: Miscellaneous construct

<400> SEQUENCE: 4

Glu Val Gln Leu Val Gln Ser Gly Ala Glu Val Lys Lys Pro Gly Glu
1               5                   10                  15

Ser Leu Lys Ile Ser Cys Lys Gly Ser Asp Phe Glu Ile Lys Asp Tyr
            20                  25                  30

Tyr Ile His Trp Val Arg Gln Met Pro Gly Lys Gly Leu Glu Trp Met
        35                  40                  45

Gly Gln Ile Asp Ala Glu Asp Gly Glu Thr Glu Tyr Ala Pro Arg Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Gly Tyr Tyr Asp Gly Arg Asp Tyr Trp Tyr Phe Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Leu Gly Thr Lys Thr Tyr Thr Cys Asn
        195                 200                 205
Val Asp His Lys Pro Ser Asn Thr Lys Val Asp Lys Arg Val Glu Ser
210                 215                 220
Lys Tyr Gly Pro Pro Cys Pro Pro Cys Pro Ala Pro Glu Phe Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser Gln
            260                 265                 270
Glu Asp Pro Glu Val Gln Phe Asn Trp Tyr Val Asp Gly Val Glu Val
        275                 280                 285
His Asn Ala Lys Thr Lys Pro Arg Glu Glu Gln Phe Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Gln Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
            420                 425                 430
His Glu Ala Leu His Asn His Tyr Thr Gln Lys Ser Leu Ser Leu Ser
        435                 440                 445
Leu Gly
    450

<210> SEQ ID NO 5
<211> LENGTH: 214
<212> TYPE: PRT
<213> ORGANISM: Artificial
<220> FEATURE:
<223> OTHER INFORMATION: Miscellaneous construct

<400> SEQUENCE: 5

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Gly Ile Gln Trp Tyr
            20                  25                  30
Leu Asn Trp Tyr Gln Gln Lys Pro Gly Lys Ala Pro Lys Leu Leu Ile
        35                  40                  45
Tyr Tyr Thr Ser Ser Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln His Ser Lys Leu Pro Arg
                85                  90                  95
Thr Phe Gly Gly Gly Thr Lys Val Glu Ile Lys Arg Thr Val Ala Ala
```

```
            100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 214
<212> TYPE: PRT
<213> ORGANISM: Artificial
<220> FEATURE:
<223> OTHER INFORMATION: Miscellaneous construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Trp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Asp Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 213
<212> TYPE: PRT
<213> ORGANISM: Artificial
```

```
<220> FEATURE:
<223> OTHER INFORMATION: Miscellaneous construct

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser Tyr Ile
            20                  25                  30

His Trp Tyr Gln Gln Lys Pro Gly Gln Ala Pro Arg Leu Leu Ile Tyr
        35                  40                  45

Ser Thr Ser Glu Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Leu Ser His Leu Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 8
<211> LENGTH: 1332
<212> TYPE: DNA
<213> ORGANISM: Artificial
<220> FEATURE:
<223> OTHER INFORMATION: Miscellaneous construct

<400> SEQUENCE: 8
caggtgcagc tggtgcagtc tggggctgag gtgaagaagc ctgggtcctc agtgaaggtt        60
tcctgcaagg catctggata cacattcact gactactttc tgaactgggt gcgacaggcc      120
cctggacaag ggcttgagtg gatgggaact atttatcctt accatgatgg tactacctac      180
tctcagaagt tcaagggcag agtcaccatt accgcggaca atccacgag cacagcctac       240 atggagctga gcagcctgag atctgaggac acggccgtgt attactgtgc gagagaggaa      300
gaggatggtc agttcgacta ctggggccaa ggaaccacgg tcaccgtctc ctcagcctcc      360
accaagggcc catcggtctt cccgctagcg ccctgctcca ggagcacctc cgagagcaca      420
gccgccctgg gctgcctggt caaggactac ttccccgaac cggtgacggt gtcgtggaac      480
tcaggcgccc tgaccagcgg cgtgcacacc ttccggctg tcctacagtc ctcaggactc      540
tactccctca gcagcgtggt gaccgtgccc tccagcagct tgggcacgaa gacctacacc      600
tgcaacgtag atcacaagcc cagcaacacc aaggtggaca gagagttga gtccaaatat      660 ggtccccat gcccacctg cccagcacct gagttcctgg ggggaccatc agtcttcctg       720
```

```
ttcccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag   1020
ccccgagagc cacaggtgta caccctgccc ccatcccagg aggagatgac caagaaccag   1080
gtcagcctga cctgcctggt caaaggcttc taccccagcg acatcgccgt ggagtgggaa   1140
agcaatgggc agccggagaa caactacaag accacgcctc ccgtgctgga ctccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gt                                                       1332
```

<210> SEQ ID NO 9
<211> LENGTH: 1332
<212> TYPE: DNA
<213> ORGANISM: Artificial
<220> FEATURE:
<223> OTHER INFORMATION: Miscellaneous construct

<400> SEQUENCE: 9

```
caggttcagc tggtgcagtc tggggctgag gtgaagaagc ctggggcctc agtgaaggtc     60
tcctgcaagg tttccggctt ccccattaag gacacctttc agcactgggt gcgacaggct    120
cctggaaaag ggcttgagtg gatgggatgg agcgatcctg agatcggtga tactgaatat    180
gcctcgaagt tccagggcag agtcaccatg accgaggaca catctacaga cacagcctac    240
atggagctga gcagcctgag atctgaggac acggccgtgt attactgtgc aacaggcgac    300
accacataca agtttgactt ctgggggcaa gggaccacgg tcaccgtctc ctcagcctcc    360
accaagggcc catcggtctt cccgctagcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacgaa gacctacacc    600
tgcaacgtag atcacaagcc cagcaacacc aaggtggaca agagagttga gtccaaatat    660
ggtcccccat gcccaccctg cccagcacct gagttcctgg ggggaccatc agtcttcctg    720
ttcccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caaagggcag   1020
ccccgagagc cacaggtgta caccctgccc ccatcccagg aggagatgac caagaaccag   1080
gtcagcctga cctgcctggt caaaggcttc taccccagcg acatcgccgt ggagtgggaa   1140
agcaatgggc agccggagaa caactacaag accacgcctc ccgtgctgga ctccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gt                                                       1332
```

```
<210> SEQ ID NO 10
<211> LENGTH: 1350
<212> TYPE: DNA
<213> ORGANISM: Artificial
<220> FEATURE:
<223> OTHER INFORMATION: Miscellaneous construct

<400> SEQUENCE: 10
gaggtgcagc tggtgcagtc tggagcagag gtgaaaaagc ccggggagtc tctgaagatc      60
tcctgtaagg gttctgactt cgagattaaa gactactata cattgggt gcgccagatg       120 cccgggaaag gcctggagtg gatggggcag attgatgctg aggatggtga aactgaatat     180
gccccgaggt tccagggcca ggtcaccatc tcagccgaca agtccatcag caccgcctac     240
ctgcagtgga gcagcctgaa ggcctcggac accgccatgt attactgtgc gagagagggt     300
tattactacg atgggcgcga ctactggtac ttcgatgtct ggggccaagg gaccacggtc     360
accgtctcct cagcctccac caagggccca tcggtcttcc cgctagcgcc ctgctccagg     420
agcacctccg agagcacagc cgccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc cagcagcttg     600
ggcacgaaga cctacacctg caacgtagat cacaagccca gcaacaccaa ggtggacaag     660
agagttgagt ccaaatatgg tcccccatgc ccacccctgcc cagcacctga gttcctgggg    720
ggaccatcag tcttcctgtt ccccccaaaa cccaaggaca ctctcatgat ctcccggacc     780
cctgaggtca cgtgcgtggt ggtggacgtg agccaggaag accccgaggt ccagttcaac     840
tggtacgtgg atggcgtgga ggtgcataat gccaagacaa agccgcggga ggagcagttc     900
aacagcacgt accgtgtggt cagcgtcctc accgtcctgc accaggactg gctgaacggc     960
aaggagtaca agtgcaaggt ctccaacaaa ggcctcccgt cctccatcga gaaaaccatc    1020
tccaaagcca aagggcagcc ccgagagcca caggtgtaca ccctgccccc atcccaggag    1080
gagatgacca agaaccaggt cagcctgacc tgcctggtca aaggcttcta ccccagcgac    1140
atcgccgtgg agtgggaaag caatgggcag ccggagaaca actacaagac cacgcctccc    1200
gtgctggact ccgacggctc cttcttcctc tacagcaggc taaccgtgga caagagcagg    1260
tggcaggagg ggaatgtctt ctcatgctcc gtgatgcatg aggctctgca caaccactac    1320
acacagaaga gcctctccct gtctctgggt                                     1350

<210> SEQ ID NO 11
<211> LENGTH: 642
<212> TYPE: DNA
<213> ORGANISM: Artificial
<220> FEATURE:
<223> OTHER INFORMATION: Miscellaneous construct

<400> SEQUENCE: 11
gacatccaga tgacccagtc tccatcctct ctgtctgcat ctgtaggaga cagagtcacc     60
atcacttgca gtgcaagtca gggcattcag tggtatttaa actggtatca gcagaaacca    120
gggaaagccc ctaagctcct gatctattac acatcaagtt tacactcagg ggtcccatca    180
aggttcagtg gcagtggatc tgggacagat ttcactctca ccatcagcag tctgcaacct    240
gaagattttg caacttacta ctgtcagcag catagtaaac ttcctcggac gttcggcgga    300
gggaccaagg tggagatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
```

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642

<210> SEQ ID NO 12
<211> LENGTH: 642
<212> TYPE: DNA
<213> ORGANISM: Artificial
<220> FEATURE:
<223> OTHER INFORMATION: Miscellaneous construct

<400> SEQUENCE: 12
gacatccaga tgacccagtc tccatcctcc ctgtctgcat ctgtaggaga cagagtcacc     60
atcacttgca aggccagtca ggatgtgcac actgctgtag cctggtatca gcagaaacca    120
gggaaagccc ctaagctcct gatctattgg gcatccaccc ggtggactgg agtcccatca    180
aggttcagtg gcagtggatc tgggacagat ttcactctca ccatcagcag tctgcaacct    240
gaagattttg caacttacta ctgtcagcaa tatagcgatt atccgtggac gttcggcgga    300
gggaccaagg tggagatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gc                      642

<210> SEQ ID NO 13
<211> LENGTH: 639
<212> TYPE: DNA
<213> ORGANISM: Artificial
<220> FEATURE:
<223> OTHER INFORMATION: Miscellaneous construct

<400> SEQUENCE: 13
gaaattgtgt tgacacagtc tccagccacc ctgtctttgt ctccagggga aagagccacc     60
ctctcctgca gtgccagctc aagtgtaagt tacatccact ggtaccaaca gaaacctggc    120
caggctccca ggctcctcat ctatagcaca tccgagctgg cttctggcat cccagccagg    180
ttcagtggca gtgggtctgg gacagacttc actctcacca tcagcagcct agagcctgaa    240
gattttgcag tttattactg tcagcagctt agtcatctcc cgctcacgtt cggcggaggg    300
accaaggtgg agatcaaacg aactgtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgc                           639

<210> SEQ ID NO 14
<211> LENGTH: 118
<212> TYPE: PRT
<213> ORGANISM: Artificial
<220> FEATURE:
<223> OTHER INFORMATION: Miscellaneous construct

<400> SEQUENCE: 14
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Phe Leu Asn Trp Val Arg Gln Ala Pro Gly Gln Gly Leu Glu Trp Met
        35                  40                  45

Gly Thr Ile Tyr Pro Tyr His Asp Gly Thr Thr Tyr Ser Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Glu Asp Gly Phe Asp Tyr Trp Gly Gln Gly Thr
                100                 105                 110

Thr Val Thr Val Ser Ser
        115

<210> SEQ ID NO 15
<211> LENGTH: 118
<212> TYPE: PRT
<213> ORGANISM: Artificial
<220> FEATURE:
<223> OTHER INFORMATION: Miscellaneous construct

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Val Ser Gly Phe Pro Ile Lys Asp Thr
            20                  25                  30

Phe Gln His Trp Val Arg Gln Ala Pro Gly Lys Gly Leu Glu Trp Met
        35                  40                  45

Gly Trp Ser Asp Pro Glu Ile Gly Asp Thr Glu Tyr Ala Ser Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Asp Thr Thr Tyr Lys Phe Asp Phe Trp Gly Gln Gly Thr
                100                 105                 110

Thr Val Thr Val Ser Ser
        115

<210> SEQ ID NO 16
<211> LENGTH: 124
<212> TYPE: PRT
<213> ORGANISM: Artificial
<220> FEATURE:
<223> OTHER INFORMATION: Miscellaneous construct

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Asp Phe Glu Ile Lys Asp Tyr
            20                  25                  30

Tyr Ile His Trp Val Arg Gln Met Pro Gly Lys Gly Leu Glu Trp Met
        35                  40                  45

Gly Gln Ile Asp Ala Glu Asp Gly Glu Thr Glu Tyr Ala Pro Arg Phe
    50                  55                  60

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Gly Tyr Tyr Asp Gly Arg Asp Tyr Trp Tyr Phe Asp
            100                 105                 110

Val Trp Gly Gln Gly Thr Thr Val Thr Val Ser Ser
        115                 120
```

<210> SEQ ID NO 17
<211> LENGTH: 107
<212> TYPE: PRT
<213> ORGANISM: Artificial
<220> FEATURE:
<223> OTHER INFORMATION: Miscellaneous construct

<400> SEQUENCE: 17

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Gln Trp Tyr
             20                  25                  30

Leu Asn Trp Tyr Gln Gln Lys Pro Gly Lys Ala Pro Lys Leu Leu Ile
         35                  40                  45

Tyr Tyr Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Ser Lys Leu Pro Arg
                 85                  90                  95

Thr Phe Gly Gly Gly Thr Lys Val Glu Ile Lys
            100                 105
```

<210> SEQ ID NO 18
<211> LENGTH: 107
<212> TYPE: PRT
<213> ORGANISM: Artificial
<220> FEATURE:
<223> OTHER INFORMATION: Miscellaneous construct

<400> SEQUENCE: 18

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val His Thr Ala
             20                  25                  30

Val Ala Trp Tyr Gln Gln Lys Pro Gly Lys Ala Pro Lys Leu Leu Ile
         35                  40                  45

Tyr Trp Ala Ser Thr Arg Trp Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Asp Tyr Pro Trp
                 85                  90                  95

Thr Phe Gly Gly Gly Thr Lys Val Glu Ile Lys
            100                 105
```

<210> SEQ ID NO 19
<211> LENGTH: 106
<212> TYPE: PRT
<213> ORGANISM: Artificial

-continued

```
<220> FEATURE:
<223> OTHER INFORMATION: Miscellaneous construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Ile
                20                  25                  30

His Trp Tyr Gln Gln Lys Pro Gly Gln Ala Pro Arg Leu Leu Ile Tyr
            35                  40                  45

Ser Thr Ser Glu Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Leu Ser His Leu Pro Leu Thr
                85                  90                  95

Phe Gly Gly Gly Thr Lys Val Glu Ile Lys
            100                 105

<210> SEQ ID NO 20
<211> LENGTH: 10
<212> TYPE: PRT
<213> ORGANISM: Artificial
<220> FEATURE:
<223> OTHER INFORMATION: Miscellaneous construct

<400> SEQUENCE: 20

Gly Tyr Thr Phe Thr Asp Tyr Phe Leu Asn
1               5                   10

<210> SEQ ID NO 21
<211> LENGTH: 17
<212> TYPE: PRT
<213> ORGANISM: Artificial
<220> FEATURE:
<223> OTHER INFORMATION: Miscellaneous construct

<400> SEQUENCE: 21

Thr Ile Tyr Pro Tyr His Asp Gly Thr Thr Tyr Ser Gln Lys Phe Lys
1               5                   10                  15

Gly

<210> SEQ ID NO 22
<211> LENGTH: 9
<212> TYPE: PRT
<213> ORGANISM: Artificial
<220> FEATURE:
<223> OTHER INFORMATION: Miscellaneous construct

<400> SEQUENCE: 22

Glu Glu Glu Asp Gly Gln Phe Asp Tyr
1               5

<210> SEQ ID NO 23
<211> LENGTH: 11
<212> TYPE: PRT
<213> ORGANISM: Artificial
<220> FEATURE:
<223> OTHER INFORMATION: Miscellaneous construct

<400> SEQUENCE: 23

Ser Ala Ser Gln Gly Ile Gln Trp Tyr Leu Asn
1               5                   10
```

```
<210> SEQ ID NO 24
<211> LENGTH: 7
<212> TYPE: PRT
<213> ORGANISM: Artificial
<220> FEATURE:
<223> OTHER INFORMATION: Miscellaneous construct

<400> SEQUENCE: 24

Tyr Thr Ser Ser Leu His Ser
1               5

<210> SEQ ID NO 25
<211> LENGTH: 9
<212> TYPE: PRT
<213> ORGANISM: Artificial
<220> FEATURE:
<223> OTHER INFORMATION: Miscellaneous construct

<400> SEQUENCE: 25

Gln Gln His Ser Lys Leu Pro Arg Thr
1               5

<210> SEQ ID NO 26
<211> LENGTH: 10
<212> TYPE: PRT
<213> ORGANISM: Artificial
<220> FEATURE:
<223> OTHER INFORMATION: Miscellaneous construct

<400> SEQUENCE: 26

Gly Phe Pro Ile Lys Asp Thr Phe Gln His
1               5                   10

<210> SEQ ID NO 27
<211> LENGTH: 17
<212> TYPE: PRT
<213> ORGANISM: Artificial
<220> FEATURE:
<223> OTHER INFORMATION: Miscellaneous construct

<400> SEQUENCE: 27

Trp Ser Asp Pro Glu Ile Gly Asp Thr Glu Tyr Ala Ser Lys Phe Gln
1               5                   10                  15

Gly

<210> SEQ ID NO 28
<211> LENGTH: 9
<212> TYPE: PRT
<213> ORGANISM: Artificial
<220> FEATURE:
<223> OTHER INFORMATION: Miscellaneous construct

<400> SEQUENCE: 28

Gly Asp Thr Thr Tyr Lys Phe Asp Phe
1               5

<210> SEQ ID NO 29
<211> LENGTH: 11
<212> TYPE: PRT
<213> ORGANISM: Artificial
<220> FEATURE:
<223> OTHER INFORMATION: Miscellaneous construct

<400> SEQUENCE: 29

Lys Ala Ser Gln Asp Val His Thr Ala Val Ala
1               5                   10
```

```
<210> SEQ ID NO 30
<211> LENGTH: 7
<212> TYPE: PRT
<213> ORGANISM: Artificial
<220> FEATURE:
<223> OTHER INFORMATION: Miscellaneous construct

<400> SEQUENCE: 30

Trp Ala Ser Thr Arg Trp Thr
1               5

<210> SEQ ID NO 31
<211> LENGTH: 9
<212> TYPE: PRT
<213> ORGANISM: Artificial
<220> FEATURE:
<223> OTHER INFORMATION: Miscellaneous construct

<400> SEQUENCE: 31

Gln Gln Tyr Ser Asp Tyr Pro Trp Thr
1               5

<210> SEQ ID NO 32
<211> LENGTH: 10
<212> TYPE: PRT
<213> ORGANISM: Artificial
<220> FEATURE:
<223> OTHER INFORMATION: Miscellaneous construct

<400> SEQUENCE: 32

Asp Phe Glu Ile Lys Asp Tyr Tyr Ile His
1               5                   10

<210> SEQ ID NO 33
<211> LENGTH: 17
<212> TYPE: PRT
<213> ORGANISM: Artificial
<220> FEATURE:
<223> OTHER INFORMATION: Miscellaneous construct

<400> SEQUENCE: 33

Gln Ile Asp Ala Glu Asp Gly Glu Thr Glu Tyr Ala Pro Arg Phe Gln
1               5                   10                  15

Gly

<210> SEQ ID NO 34
<211> LENGTH: 17
<212> TYPE: PRT
<213> ORGANISM: Artificial
<220> FEATURE:
<223> OTHER INFORMATION: Miscellaneous construct

<400> SEQUENCE: 34

Gln Ile Asp Ala Glu Asp Gly Glu Thr Glu Tyr Ala Pro Arg Phe Gln
1               5                   10                  15

Gly

<210> SEQ ID NO 35
<211> LENGTH: 17
<212> TYPE: PRT
<213> ORGANISM: Artificial
<220> FEATURE:
<223> OTHER INFORMATION: Miscellaneous construct

<400> SEQUENCE: 35

Gln Ile Asp Ala Glu Asp Gly Glu Thr Glu Tyr Ala Pro Arg Phe Gln
```

```
                 1               5                  10                 15
Gly

<210> SEQ ID NO 36
<211> LENGTH: 7
<212> TYPE: PRT
<213> ORGANISM: Artificial
<220> FEATURE:
<223> OTHER INFORMATION: Miscellaneous construct

<400> SEQUENCE: 36

Ser Thr Ser Glu Leu Ala Ser
1               5

<210> SEQ ID NO 37
<211> LENGTH: 9
<212> TYPE: PRT
<213> ORGANISM: Artificial
<220> FEATURE:
<223> OTHER INFORMATION: Miscellaneous construct

<400> SEQUENCE: 37

Gln Gln Leu Ser His Leu Pro Leu Thr
1               5

<210> SEQ ID NO 38
<211> LENGTH: 322
<212> TYPE: PRT
<213> ORGANISM: Artificial
<220> FEATURE:
<223> OTHER INFORMATION: Miscellaneous construct

<400> SEQUENCE: 38

Gly Pro Ser Val Phe Pro Leu Ala Pro Cys Ser Arg Ser Thr Ser Glu
1               5                  10                 15

Ser Thr Ala Ala Leu Gly Cys Leu Val Lys Asp Tyr Phe Pro Glu Pro
                20                 25                 30

Val Thr Val Ser Trp Asn Ser Gly Ala Leu Thr Ser Gly Val His Thr
            35                 40                 45

Phe Pro Ala Val Leu Gln Ser Ser Gly Leu Tyr Ser Leu Ser Ser Val
        50                 55                 60

Val Thr Val Pro Ser Ser Ser Leu Gly Thr Lys Thr Tyr Thr Cys Asn
65                 70                 75                 80

Val Asp His Lys Pro Ser Asn Thr Lys Val Asp Lys Arg Val Glu Ser
                85                 90                 95

Lys Tyr Gly Pro Pro Cys Pro Pro Cys Pro Ala Pro Glu Phe Leu Gly
            100                105                110

Gly Pro Ser Val Phe Leu Phe Pro Pro Lys Pro Lys Asp Thr Leu Met
        115                120                125

Ile Ser Arg Thr Pro Glu Val Thr Cys Val Val Val Asp Val Ser Gln
    130                135                140

Glu Asp Pro Glu Val Gln Phe Asn Trp Tyr Val Asp Gly Val Glu Val
145                150                155                160

His Asn Ala Lys Thr Lys Pro Arg Glu Glu Gln Phe Asn Ser Thr Tyr
                165                170                175

Arg Val Val Ser Val Leu Thr Val Leu His Gln Asp Trp Leu Asn Gly
            180                185                190

Lys Glu Tyr Lys Cys Lys Val Ser Asn Lys Gly Leu Pro Ser Ser Ile
        195                200                205

Glu Lys Thr Ile Ser Lys Ala Lys Gly Gln Pro Arg Glu Pro Gln Val
```

Tyr Thr Leu Pro Pro Ser Gln Glu Met Thr Lys Asn Gln Val Ser
225                 230                 235                 240

Leu Thr Cys Leu Val Lys Gly Phe Tyr Pro Ser Asp Ile Ala Val Glu
            245                 250                 255

Trp Glu Ser Asn Gly Gln Pro Glu Asn Asn Tyr Lys Thr Thr Pro Pro
                260                 265                 270

Val Leu Asp Ser Asp Gly Ser Phe Phe Leu Tyr Ser Arg Leu Thr Val
            275                 280                 285

Asp Lys Ser Arg Trp Gln Glu Gly Asn Val Phe Ser Cys Ser Val Met
        290                 295                 300

His Glu Ala Leu His Asn His Tyr Thr Gln Lys Ser Leu Ser Leu Ser
305                 310                 315                 320

Leu Gly

<210> SEQ ID NO 39
<211> LENGTH: 970
<212> TYPE: DNA
<213> ORGANISM: Artificial
<220> FEATURE:
<223> OTHER INFORMATION: Miscellaneous construct

<400> SEQUENCE: 39
ggcccatcgg tcttcccgct agcgccctgc tccaggagca cctccgagag cacagccgcc      60
ctgggctgcc tggtcaagga ctacttcccc gaaccggtga cggtgtcgtg gaactcaggc     120
gccctgacca gcggcgtgca caccttcccg gctgtcctac agtcctcagg actctactcc     180
gctcagcagc gtggtgaccg tgccctccag cagcttgggc acgaagacct acacctgcaa     240
cgtagatcac aagcccagca acaccaaggt ggacaagaga gttgagtcca aatatggtcc     300
cccatgccca ccctgcccag cacctgagtt cctgggggga ccatcagtct tcctgttccc     360
cccaaaaccc aaggacactc tcatgatctc ccggaccccct gaggtcacgt gcgtggtggt     420
ggacgtgagc caggaagacc ccgaggtcca gttcaactgg tacgtggatg gcgtggaggt     480
gcataatgcc aagacaaagc cgcgggagga gcagttcaac agcacgtacc gtgtggtcag     540
cgtcctcacc gtcctgcacc aggactggct gaacggcaag gagtacaagt gcaaggtctc     600
caacaaaggc ctcccgtcct ccatcgagaa aaccatctcc aaagccaaag gcagccccg      660 agagccacag gtgtacaccc tgcccccatc ccaggaggag atgaccaaga accaggtcag     720
cctgacctgc ctggtcaaag gcttctaccc cagcgacatc gccgtggagt gggaaagcaa     780
tgggcagccg gagaacaact acaagaccac gcctcccgtg ctggactccg acggctcctt     840
cttcctctac agcaggctaa ccgtggacaa gagcaggtgg caggagggga atgtcttctc     900
atgctccgtg atgcatgagg ctctgcacaa ccactacaca cagaagagcc tctccctgtc     960
tctgggttga                                                            970

<210> SEQ ID NO 40
<211> LENGTH: 444
<212> TYPE: PRT
<213> ORGANISM: Artificial
<220> FEATURE:
<223> OTHER INFORMATION: Miscellaneous construct

<400> SEQUENCE: 40

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Ser Thr

-continued

```
                    20                  25                  30
Phe Met His Trp Val Lys Gln Arg Pro Asp Gln Gly Leu Glu Trp Ile
         35                  40                  45
Gly Trp Ile Asp Pro Glu Asn Gly Asp Thr Glu Tyr Ala Ser Lys Phe
     50                  55                  60
Gln Gly Lys Ala Thr Met Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
                 85                  90                  95
Thr Thr Gly Glu Ser Asn Tyr Asp Phe Asp Phe Trp Gly Leu Gly Thr
            100                 105                 110
Thr Leu Thr Val Ser Ser Ala Lys Thr Thr Pro Pro Ser Val Tyr Pro
        115                 120                 125
Leu Ala Pro Gly Thr Ala Leu Lys Ser Asn Ser Met Val Thr Leu Gly
    130                 135                 140
Cys Leu Val Lys Gly Tyr Phe Pro Glu Pro Val Thr Val Thr Trp Asn
145                 150                 155                 160
Ser Gly Ala Leu Ser Ser Gly Val His Thr Phe Pro Ala Val Leu Gln
                165                 170                 175
Ser Gly Leu Tyr Thr Leu Thr Ser Ser Val Thr Val Pro Ser Ser Thr
            180                 185                 190
Trp Pro Ser Gln Thr Val Thr Cys Asn Val Ala His Pro Ala Ser Ser
        195                 200                 205
Thr Lys Val Asp Lys Lys Ile Val Pro Arg Asn Cys Gly Gly Asp Cys
    210                 215                 220
Lys Pro Cys Ile Cys Thr Gly Ser Glu Val Ser Ser Val Phe Ile Phe
225                 230                 235                 240
Pro Pro Lys Pro Lys Asp Val Leu Thr Ile Thr Leu Thr Pro Lys Val
                245                 250                 255
Thr Cys Val Val Asp Ile Ser Gln Asp Asp Pro Glu Val His Phe
            260                 265                 270
Ser Trp Phe Val Asp Asp Val Glu Val His Thr Ala Gln Thr Arg Pro
        275                 280                 285
Pro Glu Glu Gln Phe Asn Ser Thr Phe Arg Ser Val Ser Glu Leu Pro
    290                 295                 300
Ile Leu His Gln Asp Trp Leu Asn Gly Arg Thr Phe Arg Cys Lys Val
305                 310                 315                 320
Thr Ser Ala Ala Phe Pro Ser Pro Ile Glu Lys Thr Ile Ser Lys Pro
                325                 330                 335
Glu Gly Arg Thr Gln Val Pro His Val Tyr Thr Met Ser Pro Thr Lys
            340                 345                 350
Glu Glu Met Thr Gln Asn Glu Val Ser Ile Thr Cys Met Val Lys Gly
        355                 360                 365
Phe Tyr Pro Pro Asp Ile Tyr Val Glu Trp Gln Met Asn Gly Gln Pro
    370                 375                 380
Gln Glu Asn Tyr Lys Asn Thr Pro Pro Thr Met Asp Thr Asp Gly Ser
385                 390                 395                 400
Tyr Phe Leu Tyr Ser Lys Leu Asn Val Lys Lys Glu Lys Trp Gln Gln
                405                 410                 415
Gly Asn Thr Phe Thr Cys Ser Val Leu His Glu Gly Leu His Asn His
            420                 425                 430
His Thr Glu Lys Ser Leu Ser His Ser Pro Gly Lys
        435                 440
```

```
<210> SEQ ID NO 41
<211> LENGTH: 214
<212> TYPE: PRT
<213> ORGANISM: Artificial
<220> FEATURE:
<223> OTHER INFORMATION: Miscellaneous construct

<400> SEQUENCE: 41

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Asp Val Gln Ser
65                  70                  75                  80

Glu Asp Leu Ala Asp Tyr Phe Cys Gln Gln Tyr Ser Asn Tyr Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Ser Lys Ala Asp Tyr Glu Ser His Asn Leu Tyr
            180                 185                 190

Thr Cys Glu Val Val His Lys Thr Ser Ser Pro Val Val Lys Ser
        195                 200                 205

Phe Asn Arg Asn Glu Cys
    210

<210> SEQ ID NO 42
<211> LENGTH: 450
<212> TYPE: PRT
<213> ORGANISM: Artificial
<220> FEATURE:
<223> OTHER INFORMATION: Miscellaneous construct

<400> SEQUENCE: 42

Glu Val Gln Leu Gln Gln Ser Gly Ala Glu His Val Lys Pro Gly Ala
1               5                   10                  15

Ser Val Lys Leu Ser Cys Thr Ala Ser Asp Phe Asn Ile Lys Asp Tyr
            20                  25                  30

Tyr Ile His Trp Val Lys Gln Arg Thr Ala Gln Gly Leu Glu Trp Ile
        35                  40                  45

Gly Arg Ile Asp Pro Glu Asp Gly Glu Thr Glu Tyr Ala Pro Arg Phe
50                  55                  60

Gln Gly Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95
```

```
Ala Arg Glu Gly Tyr Tyr Tyr Asp Ser Arg Asp Tyr Trp Tyr Phe Asp
                100                 105                 110
Val Trp Gly Thr Gly Thr Thr Val Thr Val Ser Ser Ala Lys Thr Thr
        115                 120                 125
Pro Pro Ser Val Tyr Pro Leu Ala Pro Gly Thr Ala Leu Lys Ser Asn
130                 135                 140
Ser Met Val Thr Leu Gly Cys Leu Val Lys Gly Tyr Phe Pro Glu Pro
145                 150                 155                 160
Val Thr Val Thr Trp Asn Ser Gly Ala Leu Ser Ser Gly Val His Thr
                165                 170                 175
Phe Pro Ala Val Leu Gln Ser Gly Leu Tyr Thr Leu Thr Ser Ser Val
            180                 185                 190
Thr Val Pro Ser Ser Thr Trp Pro Ser Gln Thr Val Thr Cys Asn Val
        195                 200                 205
Ala His Pro Ala Ser Ser Thr Lys Val Asp Lys Lys Ile Val Pro Arg
210                 215                 220
Asn Cys Gly Gly Asp Cys Lys Pro Cys Ile Cys Thr Gly Ser Glu Val
225                 230                 235                 240
Ser Ser Val Phe Ile Phe Pro Pro Lys Pro Lys Asp Val Leu Thr Ile
                245                 250                 255
Thr Leu Thr Pro Lys Val Thr Cys Val Val Val Asp Ile Ser Gln Asp
            260                 265                 270
Asp Pro Glu Val His Phe Ser Trp Phe Val Asp Asp Val Glu Val His
        275                 280                 285
Thr Ala Gln Thr Arg Pro Pro Glu Glu Gln Phe Asn Ser Thr Phe Arg
290                 295                 300
Ser Val Ser Glu Leu Pro Ile Leu His Gln Asp Trp Leu Asn Gly Arg
305                 310                 315                 320
Thr Phe Arg Cys Lys Val Thr Ser Ala Ala Phe Pro Ser Pro Ile Glu
                325                 330                 335
Lys Thr Ile Ser Lys Pro Glu Gly Arg Thr Gln Val Pro His Val Tyr
            340                 345                 350
Thr Met Ser Pro Thr Lys Glu Glu Met Thr Gln Asn Glu Val Ser Ile
        355                 360                 365
Thr Cys Met Val Lys Gly Phe Tyr Pro Pro Asp Ile Tyr Val Glu Trp
370                 375                 380
Gln Met Asn Gly Gln Pro Gln Glu Asn Tyr Lys Asn Thr Pro Pro Thr
385                 390                 395                 400
Met Asp Thr Asp Gly Ser Tyr Phe Leu Tyr Ser Lys Leu Asn Val Lys
                405                 410                 415
Lys Glu Lys Trp Gln Gln Gly Asn Thr Phe Thr Cys Ser Val Leu His
            420                 425                 430
Glu Gly Leu His Asn His His Thr Glu Lys Ser Leu Ser His Ser Pro
        435                 440                 445
Gly Lys
    450

<210> SEQ ID NO 43
<211> LENGTH: 213
<212> TYPE: PRT
<213> ORGANISM: Artificial
<220> FEATURE:
<223> OTHER INFORMATION: Miscellaneous construct

<400> SEQUENCE: 43

Glu Ile Val Leu Thr Gln Ser Pro Ala Leu Met Ser Ala Ser Pro Gly
```

-continued

```
1               5                   10                  15
Glu Lys Val Thr Met Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Ala Asp Ala Ala Pro
                100                 105                 110

Thr Val Ser Ile Phe Pro Pro Ser Thr Glu Gln Leu Ala Thr Gly Gly
        115                 120                 125

Ala Ser Val Val Cys Leu Met Asn Asn Phe Tyr Pro Arg Asp Ile Ser
    130                 135                 140

Val Lys Trp Lys Ile Asp Gly Thr Glu Arg Arg Asp Gly Val Leu Asp
145                 150                 155                 160

Ser Val Thr Asp Gln Asp Ser Lys Asp Ser Thr Tyr Ser Met Ser Ser
                165                 170                 175

Thr Leu Ser Leu Ser Lys Ala Asp Tyr Glu Ser His Asn Leu Tyr Thr
                180                 185                 190

Cys Glu Val Val His Lys Thr Ser Ser Ser Pro Val Val Lys Ser Phe
                195                 200                 205

Asn Arg Asn Glu Cys
                210
```

METHODS OF TREATMENT COMPRISING ADMINISTERING AN ANTI-SCLEROSTIN ANTIBODY

This application is a divisional of U.S. patent application Ser. No. 12/160,472, Jul. 10, 2008 now U.S. Pat. No. 7,744,874 B2, filed Jul. 10, 2008, which was a §371 national phase filing of International Application No. PCT/US2008/056527, filed Mar. 11, 2008, which claims the benefit of U.S. Provisional Application No. 60/895,813, filed Mar. 20, 2007; which is expressly incorporated herein by reference in its entirely.

The present invention is in the field of medicine, particularly in the field of antibodies directed against sclerostin. More specifically the invention relates to high affinity antibodies that specifically bind human sclerostin and therapeutic use of the antibodies for various disorders or conditions in human subjects which benefit from an increase in at least one of bone mass, bone mineral density, bone mineral content or bone strength.

Osteoporosis is a disease in which bone mineral density (BMD) is reduced, bone microarchitecture is disrupted and osteoporotic bones are at high risk of fracture. Osteoporosis remains a major cause of long term disability and mortality, particularly among the elderly. While effective treatments for osteoporosis exist in the form of lifestyle modification and pharmacotherapy, the currently available therapies are limited in number and efficacy, are often associated with undesirable side effects and are not universally acceptable to patients. A number of antiresorptive agents including calcitonin, bisphosphonates, estrogen replacement and selective estrogen receptor modulators (SERMs) prevent further bone loss, but they do not rebuild bone once it has been lost. An anabolic agent which increases bone mass and bone mineral density and restores bone architecture is available in the form of human PTH(1-34). However, this therapeutic agent requires daily subcutaneous injection, often for a year or more, resulting in less than complete patient compliance.

Sclerostin, the SOST gene product, is strongly expressed in osteocytes within bone. Due to its role as a potent negative regulator of bone formation, sclerostin is a desirable target for therapeutic intervention for disorders or conditions which would benefit from an increase in at least one of bone mass, bone mineral density, bone mineral content and bone strength, e.g., osteoporosis. Therefore, anti-sclerostin antibodies may prove useful as an anabolic approach for treating such disorders or conditions. PCT International Publication No. WO 2006/119107 discloses amino acid sequences of particular humanized anti-sclerostin antibodies in which all of the CDRs are entirely murine, i.e., not altered from the CDRs of an antibody generated in a mouse.

There is a need for an alternative anti-sclerostin antibody which binds human sclerostin with a strong binding affinity and has a low $IC_{50}$ value in a sclerostin bioactivity assay. Such an antibody would be predicted to be more therapeutically efficacious, particularly for osteoporosis, and require less frequent dosing than does PTH(1-34) or an anti-sclerostin antibody with a lesser binding affinity (i.e., a higher $K_D$) or a higher $IC_{50}$ value. There is also a need for an antibody specific to human sclerostin wherein there is a decreased risk of an immune response to the antibody evoked by a human subject administered the antibody or a decreased risk of instability while the antibody's properties of having a high binding affinity for human sclerostin and a low $IC_{50}$ value in a bioactivity assay are maintained. The anti-sclerostin antibodies of the present invention satisfy these needs and provide related advantages.

Antibodies of the invention are chimeric or humanized monoclonal antibodies, comprise a specific polypeptide sequence disclosed herein, specifically bind human sclerostin with a high binding affinity and can be used to increase at least one of bone mass, bone mineral density, bone mineral content and bone strength in a mammal, preferably a human.

In one embodiment, at least one CDR in an antibody of the invention differs in amino acid sequence from the CDR at that position present in a parent antibody, i.e., the antibody generated in a rodent (e.g., a mouse), from which the variant antibody, i.e., humanized or chimeric antibody of the invention, was derived. Preferably, such amino acid substitution(s) in a CDR sequence of an antibody of the invention results in a greater binding affinity (i.e., lower $K_D$) with human sclerostin, a lower $IC_{50}$ in a sclerostin bioactivity assay, or both, than present in the parent antibody. An amino acid substitution in a CDR sequence of an antibody of the invention from that present in the CDR of the parent antibody may result in a decreased immunogenic response to the antibody by a human administered the antibody. Furthermore, an amino acid substitution in a CDR sequence of an antibody of the invention from that present in the CDR of the parent antibody may decrease the risk of instability of the antibody, e.g., by substitution of an asparagine residue with a different amino acid thereby decreasing the risk of deamidation.

In one embodiment, an antibody of the invention specifically binds human sclerostin and comprises six CDR regions with amino acid sequences selected from the group consisting of (i) HCDR1 with SEQ ID NO: 20, HCDR2 with SEQ ID NO: 21, HCDR3 with SEQ ID NO: 22, LCDR1 with SEQ ID NO: 23, LCDR2 with SEQ ID NO: 24, and LCDR3 with SEQ ID NO: 25; (ii) HCDR1 with SEQ ID NO: 26, HCDR2 with SEQ ID NO: 27, HCDR3 with SEQ ID NO: 28, LCDR1 with SEQ ID NO: 29, LCDR2 with SEQ ID NO: 30, and LCDR3 with SEQ ID NO: 31; and (iii) HCDR1 with SEQ ID NO: 32, HCDR2 with SEQ ID NO: 33, HCDR3 with SEQ ID NO: 34, LCDR1 with SEQ ID NO: 35, LCDR2 with SEQ ID NO: 36, and LCDR3 with SEQ ID NO: 37.

In another embodiment, an antibody of the invention specifically binds human sclerostin and comprises a heavy chain variable region ("HCVR") polypeptide and a light chain variable region ("LCVR") polypeptide wherein (i) the HCVR has the amino acid sequence of SEQ ID NO: 14 and the LCVR has the amino acid sequence of SEQ ID NO: 17; (ii) the HCVR has the amino acid sequence of SEQ ID NO: 15 and the LCVR has the amino acid sequence of SEQ ID NO: 18; or (iii) the HCVR has the amino acid sequence of SEQ ID NO: 16 and the LCVR has the amino acid sequence of SEQ ID NO: 19.

In another embodiment, an antibody of the invention specifically binds human sclerostin and comprises a heavy chain polypeptide and a light chain polypeptide wherein, (i) the heavy chain polypeptide has the amino acid sequence of SEQ ID NO: 2 and the light chain polypeptide has the amino acid sequence of SEQ ID NO: 5; (ii) the heavy chain polypeptide has the amino acid sequence of SEQ ID NO: 3 and the light chain polypeptide has the amino acid sequence of SEQ ID NO: 6; or (iii) the heavy chain polypeptide has the amino acid sequence of SEQ ID NO: 4 and the light chain polypeptide has the amino acid sequence of SEQ ID NO: 7.

In one embodiment, antibodies of the invention as defined herein, preferably defined with a SEQ ID number, are further characterized as having a binding affinity ($K_D$) for human sclerostin of about 10 pM or less at 25° C. Preferred antibodies of the invention have a $K_D$ for cynomologous monkey sclerostin of about 100 pM or less at 25° C. More preferred antibodies of the invention have a binding affinity for human sclerostin of about 10 pM or less at 25° C. and a binding affinity for cynomologous monkey sclerostin of about 100 pM or less at 25° C.

In another embodiment, antibodies of the invention as defined herein, preferably defined with a SEQ ID number, are characterized by having an $IC_{50}$ of 50 nM or less in a bone specific alkaline phosphatase assay using human sclerostin. Preferably these antibodies also have a $K_D$ for human sclerostin of about 10 pM or less at 25° C. More preferably these antibodies have a $K_D$ for human sclerostin of about 10 pM or less at 25° C. and a $K_D$ for cynomologous monkey sclerostin of about 100 pM or less at 25° C.

In another embodiment, the invention provides a pharmaceutical composition comprising an antibody of the invention and a pharmaceutically acceptable carrier or diluent. Preferably the pharmaceutical composition comprises a homogeneous or substantially homogeneous population of a monoclonal antibody of the invention and a pharmaceutically acceptable carrier or diluent.

The invention embodies the use of an antibody of the invention for the preparation of a medicament. The invention further embodies the use of an antibody of the invention in a method for increasing at least one of bone mass, bone mineral density, bone mineral content or bone strength in an animal, preferably a mammalian species, more preferably a human subject.

The invention further provides a method of increasing at least one of bone mass, bone mineral density, bone mineral content or bone strength that comprises administering to a human subject in need thereof, an effective amount of an antibody of the invention.

One embodiment of the invention provides a method for treating a disease, condition or disorder, in a human subject, which benefits from an increase in at least one of bone mass, bone mineral density, bone mineral content or bone strength, including, e.g., osteoporosis, osteopenia, osteoarthritis, pain associated with osteoarthritis, periodontal disease and multiple myeloma.

The invention further embodies a method for detecting sclerostin protein in a biological sample, comprising incubating an antibody of the invention with the biological sample under conditions and for a time sufficient to permit said antibody to bind to sclerostin protein, and detecting said binding. A preferred antibody for use in such detection assay has a heavy chain polypeptide with SEQ ID NO:40 and a light chain polypeptide with SEQ ID NO: 41; a heavy chain polypeptide with SEQ ID NO: 42, and a light chain polypeptide with SEQ ID NO: 43; a heavy chain polypeptide with SEQ ID NO: 2 and a light chain polypeptide with SEQ ID NO: 5; a heavy chain polypeptide with SEQ ID NO: 3 and a light chain polypeptide with SEQ ID NO: 6; or a heavy chain polypeptide with SEQ ID NO: 4 and a light chain polypeptide with SEQ ID NO: 7.

The invention further provides isolated nucleic acid molecules encoding an antibody of the invention; a vector comprising that nucleic acid, optionally operably-linked to control sequences recognized by a host cell transformed with the vector; a host cell comprising that vector; a process for producing an antibody of the invention comprising culturing the host cell so that the nucleic acid is expressed and, optionally, recovering the antibody from the host cell culture medium.

The invention presents antibodies that specifically bind human sclerostin, neutralize or antagonize at least one human sclerostin bioactivity in vitro or in vivo and further exhibit a strong binding affinity with human sclerostin.

When used herein, the term "sclerostin" refers to the full-length human protein with the amino acid sequence shown in SEQ ID NO: 1 or to the mature form of the protein with the signal sequence removed.

The term "antibody," in reference to an anti-sclerostin antibody of the invention (or simply, "antibody of the invention"), as used herein, refers to a monoclonal antibody. A "monoclonal antibody" as used herein refers to a chimeric antibody or a humanized antibody, unless otherwise indicated. Monoclonal antibodies of the invention can be produced using e.g., recombinant technologies, phage display technologies, synthetic technologies, e.g., CDR-grafting, or combinations of such technologies or other technologies readily known in the art. "Monoclonal antibody" refers to an antibody that is derived from a single copy or clone, including e.g., any eukaryotic, prokaryotic, or phage clone, and not the method by which it is produced.

A "monoclonal antibody" or "antibody of the invention" or simply "antibody" can be an intact antibody (comprising a complete or full length Fc region), or a portion or fragment of an antibody comprising an antigen-binding portion, e.g., a Fab fragment, Fab' fragment, or F(ab')$_2$ fragment of a chimeric or humanized antibody. Particularly preferred antigen-binding fragments of an antibody of the invention retain the ability to inhibit or neutralize one or more bioactivities characteristic of a mammalian sclerostin in vivo or in vitro. For example, in one embodiment, an antigen-binding portion of an antibody of the invention can inhibit the interaction of mature human sclerostin with one or more of its ligands and/or can inhibit one or more receptor-mediated functions of human sclerostin.

Furthermore, a "monoclonal antibody" or "antibody of the invention" or simply "antibody" as used herein can be a single chain Fv fragment that may be produced by joining the DNA encoding the LCVR and HCVR with a linker sequence. (See, Pluckthun, *The Pharmacology of Monoclonal Antibodies*, vol. 113, Rosenburg and Moore eds., Springer-Verlag, New York, pp 269-315, 1994). It is understood that regardless of whether antigen-binding fragments or portions are specified, the term "antibody" as used herein includes such fragments or portions as well as single chain forms, unless indicated otherwise. As long as the protein retains the ability to specifically bind sclerostin, it is included within the term "antibody."

The term "specifically binds" as used herein refers to the situation in which one member of a specific binding pair does not significantly bind to molecules other than its specific binding partner(s) as measured by a technique available in the art, e.g., competition ELISA, BIACORE® assay or KINEXA® assay. The term is also applicable where e.g., an antigen-binding domain of an antibody of the invention is specific for a particular epitope that is carried by a number of antigens, in which case the antibody carrying the antigen-binding domain will be able to specifically bind to the various antigens carrying the epitope. The term "epitope" refers to that portion of a molecule capable of being recognized by and bound by an antibody at one or more of the antibody's antigen-binding regions.

The phrase "bioactivity," in reference to an antibody of the invention, includes, but is not limited to, epitope or antigen binding affinity, ability to neutralize or antagonize a bioactivity of sclerostin in vivo or in vitro, $IC_{50}$ in a bone specific alkaline phosphatase assay (e.g., as described in Example 2 herein) or other in vitro activity assay, the in vivo and/or in vitro stability of the antibody and the immunogenic properties of the antibody, e.g., when administered to a human subject. The aforementioned properties or characteristics can be observed or measured using art-recognized techniques including, but not limited to, ELISA, competitive ELISA, surface plasmon resonance analysis, in vitro and in vivo neutralization assays without limit, receptor binding and immunohistochemistry with tissue sections from different sources including human, primate, or any other source as the need may be.

The phrase "bioactivity" in reference to sclerostin, includes, but is not limited to, specific binding of sclerostin to another protein (e.g., a receptor or TGF-β family member), one or more receptor-mediated functions of human sclerostin, signal transduction, immunogenic properties, in vivo or in vitro stability, affecting the levels or activity of another protein in vivo or in vitro (see e.g., Example 2), sclerostin expression levels and tissue distribution.

The term "inhibit" or "neutralize" as used herein with respect to a bioactivity of an antibody of the invention means the ability to substantially antagonize, prohibit, prevent, restrain, slow, disrupt, eliminate, stop, reduce or reverse a bioactivity of sclerostin (e.g., as measured in example 2 herein).

The term "Kabat numbering" as used herein is recognized in the art and refers to a system of numbering amino acid residues which are more variable (i.e., hypervariable) than other amino acid residues in the heavy and light chain regions of an antibody (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)). The positioning of CDRs in the variable region of an antibody follows Kabat numbering or simply, "Kabat."

A polynucleotide is "operably linked" when it is placed into a functional relationship with another polynucleotide. For example, a promoter or enhancer is operably linked to a coding sequence if it affects the transcription of the sequence.

The terms "subject," and "patient," used interchangeably herein, refer to a mammal, preferably a human. In a certain embodiment, the subject is further characterized with a disease or disorder or condition that would benefit from a decreased level of sclerostin or decreased bioactivity of sclerostin.

The term "vector" refers to a nucleic acid molecule capable of transporting another nucleic acid to which it has been operably linked including, but not limited to, plasmids and viral vectors. Certain vectors are capable of autonomous replication in a host cell into which they are introduced while other vectors can be integrated into the genome of a host cell upon introduction into the host cell, and thereby, are replicated along with the host genome. Moreover, certain vectors are capable of directing the expression of genes to which they are operably linked. Such vectors are referred to herein as "recombinant expression vectors" (or simply "expression vectors"). Exemplary vectors are well known in the art.

As used herein, the expressions "cell," "host cell," and "cell culture" are used interchangeably and include an individual cell or cell culture that is a recipient of any isolated polynucleotide of the invention or any recombinant vector(s) comprising a nucleotide sequence encoding a HCVR, LCVR or antibody of the invention. A host cell includes cells transformed, transduced or infected with one or more recombinant vectors or a polynucleotide expressing a monoclonal antibody of the invention or a light chain or heavy chain thereof.

Each heavy chain of a full-length antibody is comprised of an N-terminal heavy chain variable region (herein "HCVR") and a heavy chain constant region. Each light chain of a full-length antibody is comprised of an N-terminal light chain variable region (herein "LCVR") and a light chain constant region. The HCVR and LCVR regions can be further subdivided into regions of hypervariability, termed complementarity determining regions ("CDRs"), interspersed with regions that are more conserved, termed framework regions ("FR"). The functional ability of an antibody to bind a particular antigen or epitope is largely influenced by the six CDRs present in the variable region of the antibody. Each HCVR and LCVR is composed of three CDRs (HCDR1, HCDR2 and HCDR3 in the HCVR and LCDR1, LCDR2 and LCDR3 in the LCVR) and four FRs, arranged from amino-terminus to carboxy-terminus in the following order: FR1, CDR1, FR2, CDR2, FR3, CDR3, FR4. The CDRs contain most of the residues which form specific interactions with the antigen. CDR positioning within the variable region follows Kabat.

Light chains are classified as kappa or lambda and characterized by a particular constant region as known in the art. Heavy chains are classified as gamma, mu, alpha, delta, or epsilon, and define the antibody's isotype as IgG, IgM, IgA, IgD, and IgE, respectively and several of these may be further divided into subclasses e.g., $IgG_1$, $IgG_2$, $IgG_3$, $IgG_4$. Each heavy chain type is characterized by a particular constant region with a sequence readily known in the art. Light chain constant region kappa and heavy chain constant regions $IgG_1$, $IgG_2$, $IgG_3$, $IgG_4$ are preferred constant regions in the antibodies of the invention. More preferably, the heavy chain constant region comprises a polypeptide with an amino acid sequence of SEQ ID NO: 38 as encoded by a polynucleotide with SEQ ID NO: 39. Chimeric antibodies may have constant regions of non-human origin, preferably rat or murine.

As used herein, the "antigen-binding region" or "antigen-binding portion" refers to that portion of an antibody molecule, within the variable region, which contains the amino acid residues that interact with an antigen and confer on the antibody its specificity and affinity for the antigen. This antibody portion includes the framework amino acid residues necessary to maintain the proper conformation of the antigen-binding residues.

A preferred antibody of the invention comprises six CDRs with amino acid sequences of SEQ ID NOs: 20, 21, 22, 23, 24 and 25. Another preferred antibody of the invention comprises six CDRs with amino acid sequences of SEQ ID NOs: 32, 33, 34, 35, 36 and 37. A more preferred antibody of the invention comprises six CDRs with amino acid sequences of SEQ ID NOs: 26, 27, 28, 29, 30 and 31. The CDRs of these preferred antibodies exist in the position as stated in Table 1 below. The CDRs are positioned in the variable region according to Kabat.

A preferred antibody of the invention comprises a LCVR with the amino acid sequence of SEQ ID NO 17, 18 or 19. Other preferred monoclonal antibodies of the invention comprise a HCVR with the amino acid sequence of SEQ ID NO: 14, 15 or 16. More preferably an antibody of the invention comprises a LCVR of SEQ ID NO: 17 and a HCVR of SEQ ID NO: 14. An alternative antibody of the invention comprises a LCVR of SEQ ID NO: 19 and a HCVR of SEQ ID NO:16. A more preferred antibody of the invention comprises a LCVR of SEQ ID NO: 18 and a HCVR OF SEQ ID NO: 15. Such LCVRs are preferably linked to a light chain constant region, preferably of human origin, preferably a kappa chain. Such HCVRs are preferably operably-linked to a heavy chain constant region, preferably of human origin, preferably $IgG_1$ or $IgG_4$, most preferably a heavy chain constant region comprising the sequence of SEQ ID NO:38.

One preferred antibody of the invention comprises a heavy chain polypeptide with SEQ ID NO: 2 and a light chain polypeptide with SEQ ID NO: 5. The heavy chain polypeptide with SEQ ID NO: 2 may be encoded, e.g., by a polynucleotide sequence of SEQ ID NO: 8, the light chain polypeptide with SEQ ID NO: 5 may be encoded, e.g., by a polynucleotide of SEQ ID NO: 11.

Another preferred antibody of the invention comprises a heavy chain polypeptide with SEQ ID NO: 4 and a light chain polypeptide with SEQ ID NO: 7. The heavy chain polypeptide with SEQ ID NO:4 may be encoded, e.g., by a polynucleotide sequence of SEQ ID NO: 10, the light chain polypeptide with SEQ ID NO: 7 may be encoded, e.g., by a polynucleotide of SEQ ID NO: 13.

Another preferred antibody of the invention comprises a heavy chain polypeptide with SEQ ID NO: 3 and a light chain polypeptide with SEQ ID NO: 6. The heavy chain polypeptide with SEQ ID NO:3 may be encoded by a polynucleotide sequence of SEQ ID NO: 9, the light chain polypeptide with SEQ ID NO: 6 way be encoded by a polynucleotide of SEQ ID NO: 12.

The preferred humanized antibodies of the invention are referred to herein as 86, 88 and 89. The SEQ ID NOs of their sequences are as listed in Table 1 below.

TABLE 1

| | Protein SEQ ID NOs | | | | | | | | | |
|---|---|---|---|---|---|---|---|---|---|---|
| Antibody | Heavy Chain | Light Chain | HCVR | Heavy CDR1 | Heavy CDR2 | Heavy CDR3 | LCVR | Light CDR1 | Light CDR2 | Light CDR3 |
| 86 | 2 | 5 | 14 | 20 | 21 | 22 | 17 | 23 | 24 | 25 |
| 88 | 3 | 6 | 15 | 26 | 27 | 28 | 18 | 29 | 30 | 31 |
| 89 | 4 | 7 | 16 | 32 | 33 | 34 | 19 | 35 | 36 | 37 |

Preferably an antibody of the invention wherein all six CDRs, the HCVR, the LCVR, the HCVR and the LCVR, the entire heavy chain, the entire light chain, or the entire heavy chain and the entire light chain are limited by a particular sequence as shown by a SEQ ID NO herein (see, e.g., Table 1) is further characterized by having a $K_D$ for human sclerostin at 25° C. of less than about 10 pM, 8 pM, 6 pM or 4 pM, more preferably less than about 2.2 pM. Additionally, it is preferred that such antibody is further limited by having a $K_D$ for cynomologous monkey sclerostin at 25° C. of less than about 100 pM, 90 pM or 80 pM, or more preferably less than about 75 pM.

Preferably an antibody of the invention wherein all six CDRs, the HCVR, the LCVR, the HCVR and the LCVR, the entire heavy chain, the entire light chain, or the entire heavy chain and the entire light chain are limited by a particular sequence as shown by a SEQ ID NO herein is further characterized by having an $IC_{50}$ in a bone specific alkaline phosphatase assay using human sclerostin (see, e.g., Example 2 herein) of about 50 nM or less, about 40, 35, or 30 nM or less, more preferably about 25 nM, even more preferably about 20 nM (e.g., 20.2 nM) or less.

More preferably, an antibody of the invention wherein all six CDRs, the HCVR, the LCVR, the HCVR and the LCVR, the entire heavy chain, the entire light chain, or the entire heavy chain and the entire light chain are limited by a particular sequence as shown by a SEQ ID NO herein is further characterized by having a $K_D$ for human sclerostin at 25° C. or less than about 10 pM, 8 pM, 6 pM or 4 pM, more preferably less than about 2.2 pM, and is also characterized by having an $IC_{50}$ in a bone specific alkaline phosphatase assay using human sclerostin of about 50 nM or less, about 40, 35, or 30 nM or less, more preferably about 25 nM or less, even more preferably about 20 nM (e.g., 20.2 nM) or less.

Even more preferably, an antibody of the invention wherein all six CDRs, the HCVR, the LCVR, the HCVR and the LCVR, the entire heavy chain, the entire light chain, or the entire heavy chain and the entire light chain are limited by a particular sequence as shown by a SEQ ID NO herein is further characterized by having a $K_D$ for human sclerostin at 25° C. or less than about 10 pM, 8 pM, 6 pM or 4 pM, more preferably less than about 2.2 pM; is also characterized by having an $IC_{50}$ in a bone specific alkaline phosphatase assay using human sclerostin of about 50 nM or less, about 40, 35, or 30 nM or less, more preferably about 25 nM or less, even more preferably about 20 nM (e.g., 20.2 nM) or less; and is also characterized by having an $IC_{50}$ in a bone specific alkaline phosphatase assay using cynomologous monkey sclerostin of about 75 nM or less.

Antibody Expression

The present invention is also directed to host cells that express an anti-sclerostin antibody of the invention. Creation and isolation of host cell lines producing an antibody of the invention can be accomplished using standard techniques known in the art.

A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors—one expressing the heavy chain and one expressing the light chain. Optionally the heavy chain and light chain may be expressed in different host cells.

Additionally, the recombinant expression vector can encode a signal peptide that facilitates secretion of the anti-sclerostin antibody light and/or heavy chain from a host cell. The anti-sclerostin antibody light and/or heavy chain gene can be cloned into the vector such that the signal peptide is operably linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g. $IgG_1$, $IgG_2$, $IgG_3$ and $IgG_4$) or subclass constant region and any allotypic variant thereof as described in Kabat (supra). A preferred heavy chain constant region comprises the polypeptide of SEQ ID NO:38.

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

Preferred mammalian host cells for use in the invention are CHO cells (e.g. ATCC CRL-9096), NS0 cells, SP2/0 cells and COS cells (ATCC e.g., CRL-1650, CRL-1651), HeLa (ATCC CCL-2). Additional host cells for use in the invention include other mammalian cells, yeast cells and prokaryotic cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the host cell and/or the culture medium using standard purification methods.

Once expressed, the intact antibodies, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90%, 92%, 94% or 96% homogeneity are preferred, and 98 to 99% or more homogeneity most preferred, for pharmaceutical uses. Once purified, partially or to homogeneity as desired, the sterile antibodies may then be used therapeutically, as directed herein.

Humanized Antibody

Preferably an antibody of the invention to be used for therapeutic purposes, has the sequence of the framework and constant region (to the extent it exists in the antibody) derived from the mammal in which it would be used as a therapeutic so as to decrease the possibility that the mammal would illicit an immune response against the therapeutic antibody. Humanized antibodies are of particular interest since they are valuable for therapeutic application and diminish the likelihood of a human anti-mouse antibody response frequently observed with antibodies of murine origin or antibodies comprising portions which are of murine origin when administered to a human subject. Preferably injected humanized antibodies may have a half-life more like that of naturally occurring human antibodies than do e.g., murine antibodies, thereby allowing smaller and less frequent doses to be administered to a subject.

The term "humanized antibody" as used herein refers to an antibody wherein at least one portion is of human origin. For example, the humanized antibody can comprise portions derived from an antibody of nonhuman origin, such as a mouse, and portions derived from an antibody of human origin, joined together, e.g., chemically by conventional techniques (e.g., synthetic) or prepared as a contiguous polypeptide using genetic engineering techniques.

Preferably, a "humanized antibody" has CDRs that originate from or are derived from a parent antibody, i.e., a non-human antibody (preferably a mouse monoclonal antibody), while framework and constant region, to the extent it is present, (or a significant or substantial portion thereof, i.e., at least about 90%, 92%, 94%, 95%, 96%, 97%, 98% or 99%) are encoded by nucleic acid sequence information that occurs in the human germline immunoglobulin region (see, e.g., the International ImMunoGeneTics Database) or in recombined or mutated forms thereof whether or not said antibodies are produced in a human cell. Preferably, at least two, three, four, five or six CDRs of a humanized antibody are optimized from the CDRs of a non-human parent antibody from which the humanized antibody was derived, to generate a desired property, e.g., improved specificity, affinity or neutralization, which may be identified by a screening assay, e.g., an ELISA assay. Preferably an optimized CDR in an antibody of the invention comprises at least one amino acid substitution when compared to that present in the parent antibody. Certain amino acid substitutions in the CDRs of humanized antibodies 88 and 89 of the invention as compared to those of parent antibodies 788 and 789 (see examples 5 and 6 herein) decrease the likelihood of instability of the antibody (e.g., removal of CDR Asn residues) or decrease the likelihood of immunogenicity of the antibody when administered to a human subject (e.g., as predicted by IMMUNOFILTER™ Technology).

Humanized antibodies preferably contain minimal sequence derived from a non-human antibody. Humanized antibodies may comprise residues which are found neither in the recipient antibody nor in the CDR or framework sequences imported from the parent antibody. Humanized antibodies may be subjected to in vitro mutagenesis using methods of routine use in the art and, thus, the framework region amino acid sequences of the HCVR and LCVR regions of the humanized recombinant antibodies are sequences that, while derived from those related to human germline HCVR and LCVR sequences, may not naturally exist within the human antibody germline repertoire in vivo. It is contemplated that such amino acid sequences of the HCVR and LCVR framework regions of the humanized recombinant antibodies are at least 90%, 92%, 94%, 95%, 96%, 98% or more preferably at least 99% or most preferably 100% identical to a human germline sequence.

In preferred embodiments, a humanized antibody of the present invention comprises human germline light chain framework sequences (see, e.g., PCT WO 2005/005604) and human germline heavy chain framework sequences (see, e.g., PCT WO 2005/005604). Preferred human germline light chain framework regions are from a human kappa light chain gene selected from the group consisting of: A11, A17, A18, A19, A20, A27, A30, L1, L11, L12, L2, L5, L6, L8, O12, O2, and O8. Preferred human germline heavy chain framework regions are from a human heavy chain selected from the group consisting of: VH2-5, VH2-26, VH2-70, VH3-20, VH3-72, VH1-24, VH1-46, VH3-9, VH3-66, VH3-74, VH4-31, VH1-18, VH1-69, VH3-7, VH3-11, VH3-15, VH3-21, VH3-23, VH3-30, VH3-48, VH4-39, VH4-59, VH5-51 (see, International Publication No. WO2006/046935).

There are multiple methods available in the art to generate humanized antibodies. For example, humanized antibodies may be produced by obtaining nucleic acid sequences encoding the HCVR and LCVR of a parent antibody (e.g., a murine antibody or antibody made by a hybridoma) which specifically binds sclerostin, preferably human sclerostin, identifying the CDRs in said HCVR and LCVR (nonhuman), and grafting such CDR-encoding nucleic acid sequences onto selected human framework-encoding nucleic acid sequences. Optionally, a CDR region may be optimized by mutagenizing randomly or at particular locations in order to substitute one or more amino acids in the CDR with a different amino acid prior to grafting the CDR region into the framework region. Alternatively, a CDR region may be optimized subsequent to insertion into the human framework region using methods available to one of skill in the art.

After the CDR-encoding sequences are grafted onto the selected human framework encoding sequences, the resultant DNA sequences encoding the humanized variable heavy and variable light sequences are then expressed to produce a humanized antibody that binds sclerostin. The humanized HCVR and LCVR may be expressed as part of a whole anti-sclerostin antibody molecule, i.e., as a fusion protein with human constant domain sequences. However, the HCVR and LCVR sequences can also be expressed in the absence of constant sequences to produce a humanized anti-sclerostin Fv.

References further describing methods involved in humanizing a mouse antibody that may be used include e.g., Queen et al., *Proc. Natl. Acad. Sci. USA* 88:2869, 1991 and the method of Winter and co-workers [Jones et al., Nature, 321: 522 (1986); Riechmann et al., Nature, 332:323-327 (1988); Verhoeyen et al., Science, 239:1534 (1988)].

Diagnostic Uses

An antibody of the invention may be used to diagnose a disorder or disease associated with the expression of human sclerostin. In a similar manner, the antibody of the invention can be used in an assay to monitor sclerostin levels in a subject being treated for a sclerostin-associated condition. Such applications include methods that utilize an antibody of the invention and a label to detect sclerostin in a biological sample, e.g., in a human body fluid or in a cell or tissue extract (see, e.g., Example 1 herein). Antibodies of the invention may be used with or without modification, and may be labeled by covalent or non-covalent attachment of a detectable moiety.

A variety of conventional protocols for measuring sclerostin levels in a biological sample, including e.g., ELISAs, RIAs, and FACS, are known in the art and provide a basis for diagnosing altered or abnormal levels of sclerostin expression. Normal or standard sclerostin levels present in a sample are established using any known technique, e.g., by combining a sample comprising a sclerostin polypeptide with, e.g., an antibody of the invention under conditions suitable to form an antigen:antibody complex. The antibody is directly or indirectly labeled with a detectable substance to facilitate detection of the bound or unbound antibody. Suitable detectable substances include various enzymes, prosthetic groups, fluorescent materials, luminescent materials and radioactive materials. The amount of a standard complex formed is quantitated by various methods, such as, e.g., photometric means. Amounts of sclerostin polypeptide present in samples are then compared with the standard values.

Therapeutic Uses

Sclerostin functions as a negative regulator of bone formation. (see, e.g., Cytokine & Growth Factor Reviews, 16:319-327, 2005). In adults, sclerostin mRNA is primarily detected in osteocytes although lower concentrations have been found by Applicants in cartilage.

A pharmaceutical composition comprising an anti-sclerostin monoclonal antibody of the invention may be used to increase at least one of bone mass, bone mineral density, bone mineral content or bone strength in either vertebral or non-vertebral bone, or both, when an effective amount is administered to a human subject in need thereof. A pharmaceutical composition comprising an anti-sclerostin monoclonal antibody of the invention may be used to reduce the incidence of fracture of vertebral and/or non-vertebral bone, when an effective amount is administered to a human subject in need thereof. Reducing the incidence of fracture includes reducing the likelihood or actual incidence of fracture for a human subject compared to an untreated control population.

Furthermore, an antibody of the invention may be useful for the treatment of conditions, diseases, or disorders wherein the presence of sclerostin causes or contributes to undesirable pathological effects or a decrease of sclerostin levels or sclerostin bioactivity has a therapeutic benefit in human subjects. Such conditions, diseases or disorders include, but are not limited to, osteoporosis, osteopenia, osteoarthritis, pain associated with osteoarthritis, periodontal disease or multiple myeloma. Subjects may be male or female. Preferably a human subject is at risk of fracture of vertebral and/or non-vertebral bone, more preferably a human subject is at risk for, or suffering from, osteoporosis. The human subject is preferably a female and more preferably a female at risk for or having post-menopausal osteoporosis. It is contemplated that the method of the invention can benefit a subject at any stage of osteoporosis.

Additionally, the use of an antibody of the invention for use in the manufacture of a medicament for the treatment of at least one of the aforementioned disorders is contemplated.

The terms "treatment" and "treating" are intended to refer to all processes wherein there may be a slowing, interrupting, arresting, controlling, or stopping of the progression of the disorders described herein, but does not necessarily indicate a total elimination of all disorder symptoms. "Treatment", as used herein, includes administration of a compound of the present invention for treatment of a disease or condition in a mammal, particularly in a human, and includes: (a) inhibiting further progression of the disease, i.e., arresting its development; and (b) relieving the disease, i.e., causing regression of the disease or disorder or alleviating symptoms or complications thereof. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation.

Pharmaceutical Composition

An antibody of the invention can be incorporated into a pharmaceutical composition suitable for administration to a human subject. An antibody of the invention may be administered to a human subject alone or in combination with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington, The Science and Practice of Pharmacy*, $19^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with a monoclonal antibody of the invention, retains the molecule's activity and is non-reactive with the subject's immune system.

A pharmaceutical composition comprising an anti-sclerostin monoclonal antibody of the present invention can be administered to a subject at risk for or exhibiting pathologies as described herein, e.g., osteoporosis, osteoarthritis or other bone degenerative disorders, using standard administration techniques.

A pharmaceutical composition of the invention preferably contain an "effective amount" of an antibody of the invention. An effective amount refers to an amount necessary (at dosages and for periods of time and for the means of administration) to achieve the desired therapeutic result. An effective amount of the antibody may vary according to factors such as the disease state, age, sex, and weight of the individual, and the ability of the antibody or antibody portion to elicit a desired response in the individual. An effective amount or is also one in which any toxic or detrimental effect of the antibody, are outweighed by the therapeutically beneficial effects.

An effective amount is at least the minimal dose, but less than a toxic dose, of an active agent which is necessary to impart therapeutic benefit to a subject. Stated another way, an effective amount or therapeutically effective amount of an antibody of the invention is an amount which in mammals, preferably humans, (i) increases at least one of bone mass, bone mineral density, bone mineral content or bone strength, or (ii) treats a condition, disorder or disease wherein the presence of sclerostin causes or contributes to an undesirable pathological effect, or (iii) a decrease in sclerostin levels or sclerostin bioactivity results in a beneficial therapeutic effect in a mammal, preferably a human, including, but not limited to osteoporosis, osteopenia, osteoarthritis, rheumatoid arthritis, periodontal disease or multiple myeloma.

As is well known in the medical arts, dosages for any one subject depends upon many factors, including the patient's size, body surface area, age, the particular compound to be administered, sex, time and route of administration, general health, and other drugs being administered concurrently. Dose may further vary depending on the type and severity of the disease. A typical dose can be, for example, in the range of 0.001 to 1000 µg; preferably 1 to 100 µg; however, doses below or above this exemplary range are envisioned, especially considering the aforementioned factors. A daily parenteral dosage regimen can be about 0.1 µg/kg to about 20 mg/kg of total body weight, preferably from about 0.3 µg/kg to about 10 mg/kg. Progress may be monitored by periodic assessment, and the dose adjusted accordingly.

These suggested amounts of antibody are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the antibody, the particular type of antibody, the method of administration, the scheduling of administration, and other factors known to medical practitioners.

The route of administration of an antibody of the present invention may be oral, parenteral, by inhalation, or topical. Preferably, the antibodies of the invention can be incorporated into a pharmaceutical composition suitable for parenteral administration. The term parenteral as used herein includes intravenous, intramuscular, subcutaneous, rectal, vaginal, or intraperitoneal administration. Parenteral delivery by intravenous or intraperitoneal or subcutaneous injection is preferred. Subcutaneous injection is most preferred. Suitable vehicles for such injections are well known in the art.

The pharmaceutical composition typically must be sterile and stable under the conditions of manufacture and storage in the container provided, including e.g., a sealed vial, syringe or other delivery device, e.g., a pen. Therefore, pharmaceutical compositions may be sterile filtered after making the formulation, or otherwise made microbiologically acceptable.

The following examples are offered for illustrative purposes only, and are not intended to limit the scope of the present invention.

EXAMPLES

Example 1

ELISA Assay

This assay is used to detect and quantify sclerostin in human serum samples to a lower detection limit of 0.4 ng/ml. Antibody 86 is the capture antibody, while antibody 88 is the detection antibody (see table 1 for antibody sequences).

The inner wells of a 96-well plate are coated with 100 µl of full-length anti-sclerostin monoclonal antibody 86 at a concentration of 0.5 µg/mL in 0.5 M sodium carbonate at pH 9.6 ("coating buffer"). The plate is sealed and incubated overnight at 4° C. The plate is then washed three times with TBST "wash buffer" (0.4 M Tris-HCl, 3M NaCl, 0.1% Tween 20). Then 200 µL of casein blocking buffer in PBS (Pierce, #37528) is added per well and the plate is incubated for one hour at room temperature. The plate is then washed twice in wash buffer to remove the blocking solution.

To generate a standard curve, human sclerostin at a concentration of 0.35 mg/mL is prepared in casein blocking buffer and serially diluted two fold (from 1.25 ng/ml to 0 ng/ml) in 5% pooled human serum in casein blocking buffer in PBS. The human serum is run over a column of magnetic beads coated with anti-sclerostin monoclonal antibody 86 to remove any sclerostin that may have been endogenously present in the serum.

One hundred microliters of samples (5% serum in casein blocking buffer) or standards are added to wells in duplicate and the plate is further incubated at room temperature for two hours. The wells are then washed 5 times with wash buffer.

One hundred microliters of detection antibody (full-length anti-sclerostin monoclonal antibody 88) which has been biotinylated with Pierce EZ link NHS-LC biotin kit is added per well. The plate is incubated at room temperature for one hour and then washed four times with wash buffer. Streptavidin-horseradish peroxidase is diluted 1:2000 in casein blocking buffer in PBS to a final concentration of 0.5 µg/ml, then 100 µL is added per well, incubated at room temperature for one hour and then washed 7 times with wash buffer. OPD substrate (Sigma P8806) is added at 100 µL/well and reaction is allowed to continue at room temperature for 20 minutes. The reaction is then terminated by adding 100 µL/well of 1 N HCl. The plate is read at OD 490 nm.

Example 2

Neutralization

Bone Specific Alkaline Phosphatase Assay

Bone specific alkaline phosphatase is a biochemical indicator of osteoblast activity. The bone specific alkaline phosphatase assay described herein is based on the ability of sclerostin to decrease BMP-4 and Wnt3a-stimulated alkaline phosphatase levels in the multipotential murine cell line, C2C12, while an antibody which neutralizes sclerostin activity would result in a dose-dependent increase of alkaline phosphatase activity in this assay. Wnt3a and BMP-4 are osteogenic growth factors.

C2C12 cells (ATCC, CRL 1772) are plated at 3000-5000 cells per well in a 96-well tissue culture plate in MEM medium supplemented with 5% fetal calf serum, then incubated at 37° C. in 5% $CO_2$ overnight. The antibody to be tested is diluted in 0.5× Wnt3a-conditioned medium to various final concentrations. The medium is then removed from the cells on the tissue culture plate and 150 μl per well of a pre-mixed antibody-BMP4-sclerostin solution (human or cynomologous monkey) is added in which the antibody is at a final concentration 30 μg/ml to 0.5 μg/ml, BMP-4 is at a final concentration of 25 ng/ml and the sclerostin protein is at a final concentration of 1.0 μg/ml and the conditioned medium is at 0.5× concentration. The plate is then incubated at 37° C. in 5% $CO_2$ for 72 hours. The medium is removed from the cells on the tissue culture plate, the cells are washed once with PBS, then the plate of cells is frozen and thawed three times alternating between −80° C. and 37° C.

The Wnt3a conditioned media is prepared by growing L-Wnt-3A cells and control L-cells (ATCC CRL-2647 and CRL-2648, respectively) for four days, from a 1:20 split of confluent cells, in DMEM with 10% FBS and 2 mM L-glutamine. The collected media is filtered through 0.2 micron nylon membranes and stored at −20° C. long term or 4° C. short term.

Alkaline phosphatase activity is measured by adding 150 μl per well of alkaline phosphatase substrate (1-step PNPP, Pierce #37621). The plate of cells is then incubated for 60 minutes at room temperature at which time OD at 405 nm is read to determine the alkaline phosphatase activity. Antibody neutralization $IC_{50}$ values reported in Table 2 below are averages from 2 separate experiments. The $IC_{50}$ calculations are performed using SigmaPlot Regression Wizard with a Sigmoid 4-parameter fit equation.

TABLE 2

| Antibody | $IC_{50}$ (nM) Using Human sclerostin | $IC_{50}$ (nM) Using Cyno sclerostin |
|---|---|---|
| 89 | 25.1 | 34.4 |
| 88 | 20.2 | 23.7 |
| 86 | 25.5 | 31.6 |

Example 3

Affinity Binding

Equilibrium binding studies between an anti-sclerostin antibody and either human, cynomologous ("cyno") monkey or rat sclerostin are performed on a KinExA 3000 instrument (Sapidyne Instruments Inc.) under $K_D$-controlled conditions. With this technique, a fixed concentration of antibody below its $K_D$ is mixed with various concentration of sclerostin protein and allowed to come to equilibrium. The fraction of free, unbound, antibody remaining in solution is probed by briefly exposing this equibrated mixture to sclerostin-coated beads followed by detection with a fluorescently labeled secondary antibody. Typically 2 pM of an anti-sclerostin antibody to be tested is mixed with varying concentrations of human, cyno, or rat sclerostin starting at 2-50 nM and doing three-fold serial dilutions in binding buffer (1× phosphate buffered saline solution, pH 7.4, 0.02% sodium azide and 1 mg/mL bovine serum albumin) containing 2 pM of the antibody to be tested. These solutions are allowed to reach equilibrium over two days at 25° C. The amount of unbound antibody is probed using human sclerostin-coated azlactone beads (Sapidyne Instruments Inc.). These beads are prepared by reacting 50 mg of dry azlactone beads with 50 mcg/ml human sclerostin in a 50 mM sodium carbonate buffer at pH 9.0-9.6 with overnight rotation. Beads are then allowed to settle and the supernatant is replaced with blocking solution (1 M Tris, pH 8.0, plus 10 mg/mL bovine serum albumin) and rotated for one hour. This bead stock is diluted 20-fold into binding buffer and used within three days. A KinExA 3000 instrument equilibrated at room temperature (ca 25° C.) is used for binding studies. Typically 6.25 mL of the equilibrated antibody/sclerostin solution are drawn over a packed human sclerostin-azlactone bead column at 0.25 mL/minute flow rate then rinsed with running buffer (1× phosphate buffered saline solution, pH 7.4 with 0.02% sodium azide). The fraction of free anti-sclerostin antibody bound to these beads is quantified by measuring fluorescence resulting from an injected labeled secondary antibody (Cy5-labeled goat anti-human Fab'2 antibody). Two replicate samples for each condition are analyzed and $K_D$ is determined by fitting data to a 1:1 binding model using KinExA Pro software. The average of the $K_D$ values at 25° C. are reported in Table 3 below.

TABLE 3

| | Affinity | | |
|---|---|---|---|
| Antibody | Human Sclerostin $K_D$ (pM) | Rat Sclerostin $K_D$ (pM) | Cyno Sclerostin $K_D$ (pM) |
| 89 | 0.3 | 0.4 | 1.4 |
| 88 | 2.2 | 2.2 | 75 |
| 86 | 0.6 | 0.1 | 1.0 |

Example 4

In Vivo Calcein Assay

The rat calcein assay allows direct evaluation of bone formation over a short (10 day) period of time and the effect of an antibody of the invention on bone formation. Calcein is a fluorochrome label which is incorporated into the bone matrix during new bone formation. Quantitative measurement of calcein reflects the degree of bone formation induced by pharmacologic agents. Six month old female Sprague-Dawley rats are used (n=6/dose group). Rats are dosed every 3 days by subcutaneous injection (days 0, 3, and 6) with 1 mg/kg or 6 mg/kg antibody in PBS vehicle, or with 10 μg/kg PTH daily or with 6 mg/kg human IgG as a negative control. Calcein is injected subcutaneously on day 7 and rats are sacrificed on day 10. Tibiae are collected and cut to evaluate trabecular bone formation (distal metaphysis) or cortical bone formation (tibial diaphysis) and subjected to demineralization and fluorochrome quantitation of total calcein. The values shown in Table 4 below are averages with the human IgG control set to 1.0. The data demonstrate that administration of antibodies of the invention leads to both trabecular and cortical bone formation.

TABLE 4

| Antibody | Dose mg/kg | Relative Trabecular Calcein | Relative Cortical Calcein |
|---|---|---|---|
| Hu IgG | 6 | 1.00 | 1.00 |
| PTH | .01 | 1.45 | 1.89 |
| 89 | 6 | 1.97 | 1.88 |

TABLE 4-continued

| Antibody | Dose mg/kg | Relative Trabecular Calcein | Relative Cortical Calcein |
|---|---|---|---|
| 88 | 6 | 1.90 | 2.18 |
| 86 | 6 | 1.77 | 2.78 |

Example 5

Osteoarthritis

SOST expression is mainly confined to bone tissue. However, applicants determine herein that another tissue with significant SOST expression is cartilage as measured by real-time PCR. Cartilage expression of SOST is also observed using an array of RNA isolated from cartilage of normal or osteoarthritic patients. Furthermore, in the array, expression of SOST increases relative to osteoarthritis severity such that expression in cartilage from mild osteoarthritis is greater than control, severe is greater than mild, and severe surgical (removed for knee replacement surgery) is greater than all others demonstrating a correlation of osteoarthritis and SOST expression. An antibody specific to sclerostin may be used to treat osteoarthritis.

An anti-sclerostin chimeric antibody with a murine variable region on a rat Fc region, antibody 789 with SEQ ID NO:42 for heavy chain and SEQ ID NO:43 for light chain, is tested for the ability to block joint pain in the MIA model of osteoarthritis. The variable region of this antibody was the parent sequence for generation of the humanized antibody 89 (HCVR with SEQ ID NO: 16 and LCVR with SEQ ID NO: 19). Both, humanized antibody 89 and chimeric antibody 789 bind the same epitope. This osteoarthritis model utilizes monoiodoacetate (MIA) injections directly into the knee joint to induce an OA-like process that involves an inflammatory and cytokine mediated pain and cartilage destruction process. The contralateral knee of a rat is injected with saline only, and pain is measured as the difference in weight-bearing of the 2 hind legs.

MIA experiment #1 utilizes young male Lewis rats (7-8 weeks of age) in "prevention mode" where the anti-sclerostin antibody is administered prior to MIA injections. The day prior to MIA injections, rats are injected with either 10 mg/kg anti-sclerostin antibody i.p. or 10 mg/kg control IgG, or PBS (n=6 per group). The following day, rats are anesthetized and the right knees are injected with 0.3 mg of monosodium iodoacetate dissolved in 50 ul of 0.9% sterile saline. The left knees are injected with saline alone. Injections are through the patellar ligament using an insulin syringe with a 28G needle covered with a plastic tubing sheath to allow only 5 mm penetration into the knee joint.

Pain measurements are taken 2 and 7 days after MIA injection (3 and 8 days after antibody injection). After the pain measurement on day 7, a second dose of the antibody or control injection is administered. Additional pain measurements are then taken 10 and 14 days after MIA (3 and 7 days after the second injection of the antibody).

Pain is measured by difference in weight bearing of the injected legs through use of an incapacitance tester. Rats are placed in a Perspex box with their hind paws on the pressure sensors. When the rats are reliably still, a 1 second reading is taken, followed by 2 additional readings and the average calculated. The weight placed on the MIA-injected leg is subtracted from the saline-injected leg to give the difference in weight bearing.

A statistically significant decrease in pain is seen with the anti-sclerostin antibody compared to IgG (and PBS) control at days 7, 10 and 14 after MIA administration (Table 5 below). Values are weight bearing differences between MIA injected leg and saline injected leg in grams (standard error of the mean).

A second MIA experiment is carried out with older rats (27 weeks of age) and in "treatment mode" where antibody is administered after MIA is injected. Rats receive MIA or control saline injections as before and then 6 days later 10 mg/kg anti-sclerostin antibody, control IgG, or PBS (n=6 per group) are injected i.p. On days 8 and 15 after MIA (2 and 9 days after antibody) pain measurements are taken as before. On day 16 after MIA, a second dose of the anti-sclerostin antibody and controls is administered, and on day 21 (5 days after second antibody dose) pain measurements are again collected.

At the early timepoint after administration of the anti-sclerostin antibody (day 8 post-MIA) there is no effect of the antibody on pain, but 7 days later, there is a trend towards decreased pain as measured by weight bearing differences between MIA injected leg and saline injected leg in grams. The trend towards reduced pain with anti-sclerostin antibody is also seen 5 days after the second antibody dosing. Chimeric antibody 789 differed from IgG control with a p-value of 0.06 and 0.08 at day 15 and 21 respectively. Together, these results demonstrate that joint pain resulting from the established MIA disease process is interrupted by administering neutralizing anti-sclerostin antibody.

Example 6

OVX Rat Studies

The ovariectomized (OVX) rat is a well recognized model for post-menopausal osteoporosis. In this study the effects of anti-sclerostin antibodies of the invention comprising a murine variable region and a rat Fc are examined in the OVX rat.

Six month old female Sprague-Dawley rats are ovariectomized and allowed to lose bone for 1 month prior to dosing. One group of rats (n=8) are not ovariectomized but are sham-operated for bone comparison to ovariectomized rats. All OVX rats are randomized into treatment groups (n=7 each) and treated with either PTH (1-38), IgG control (10 mg/kg) or 10 mg/kg of chimeric anti-sclerostin antibody (Antibody 788 with heavy chain of SEQ ID NO: 40 and light chain of SEQ ID NO:41 [the variable region of this antibody was the parent sequence for generation of the humanized antibody 88]; Antibody 789 with heavy chain of SEQ ID NO: 42 and light chain of SEQ ID NO: 43) for a total of 58 days. The antibodies are all dosed subcutaneously once every 3 days, while the PTH (1-38) is dosed daily subcutaneously at 10 mg/kg. Upon sacrifice, the femurs and vertebrae are removed for quantitative computed tomography (CT) analysis using a CT scanner to measure the distal femur (trabecular bone) and midshaft (cortical bone) as well as the $5^{th}$ lumbar vertebrae. Bones are positioned on molding clay for reproducible measurements and scans of the femurs are taken 2 mm from the end of the epiphysis (distal femur) or 10 mm from the epiphysis (midshaft femur).

Vertebral measurements are done with L-5 scanned from a landmark "V" structure in the vertebra. Data are calculated by manufacture software package SYS-C320-V 1.5. The biomechanical properties of the femoral diaphysis, the L-5 vertebrae and femoral neck are measured post-necropsy according to: Turner C H, Burr D B, Basic biomechanical measurements of bone: a tutorial. Bone 14(4):595-608, 1993. Mechanical properties of the midshaft are measured for intact left femora using 3-point bending with load applied midway between two supports 15 mm apart. Femora are positioned so the loading point is about 7.5 mm proximal from the distal popliteal space and bending occurs about the medial-lateral axis. Specimens are tested in a saline bath at 37° C. Load-displacement curves are recorded at a crosshead speed of 10 mm/min using a materials testing machine (model: 1/S, MTS Corp, Minneapolis, Minn.) and analyzed using TestWorks 4 software (MTS Corp.) to calculate peak load. Mechanical properties of L-5 vertebrae were analyzed after the posterior processes were removed and the ends of the centrum were made parallel using a diamond wafering saw (Buehler Isomet, Evanston, Ill.). Vertebral specimens are loaded in compression, using the materials testing device and analyzed using TestWorks 4 software (MTS Corp.). For femoral neck measurements, the femur is positioned vertically in a mounting chuck with the proximal side up and load was applied downward on the midpoint of the femoral head. Analysis was with TestWorks 4 software (MTS Corp.). The average values and standard error of the mean values are in Table 5 and 6 below. The data demonstrate that chimeric antibodies 788 and 789 increase bone mineral density ("BMD"), bone mineral content ("BMC") and bone strength (peak load) in OVX rats.

TABLE 5

| Treatment | Dist. Femur BMD (mg/cm$^3$) | Dist. Femur BMC (mg) | Mid Femur BMD (mg/cm$^3$) | Mid Femur BMC (mg) | Vertebral BMD (mg/cm$^3$) | Vertebral BMC (mg) |
|---|---|---|---|---|---|---|
| Sham | *602 | 74.1 | 898 | 61.2 | *587 | 165 |
| IgG | 528 | 68.6 | 852 | 60.5 | 526 | 149 |
| PTH | *744 | *95.3 | *925 | 63.2 | *642 | *180 |
| 788 | *675 | *91.4 | *946 | *68.6 | *703 | *209 |
| 789 | *710 | *94.9 | *951 | *68.4 | *721 | *209 |

*Statistically significant increase from IgG control, p < 0.05, Dunnett's Method.

TABLE 6

| Treatment | Femoral Neck Peak Load (Newtons) | Mid Femur Peak Load (Newtons) | Vertebral Peak Load (Newtons) |
|---|---|---|---|
| Sham | 96.5 | 134 | 236 |
| IgG | 100.4 | 126 | 188 |
| PTH | 117.6 | 128 | *328 |
| 2492788 | *131.6 | *147 | *431 |
| 2492789 | *147.5 | *153 | *432 |

*Statistically significant increase from IgG control, p < 0.05, Dunnett's Method.

We claim:

1. A method of treating a disease or disorder selected from the group consisting of osteoporosis, osteopenia, osteoarthritis, and pain associated with osteoarthritis in a human subject in need thereof, comprising administering to said human subject an effective amount of an antibody or antigen-binding portion thereof, that binds human sclerostin and comprises a heavy chain variable region and a light chain variable region, wherein:

i) the heavy chain variable region has the amino acid sequence of SEQ ID NO: 14, and the light chain variable region has the amino acid sequence of SEQ ID NO: 17; or ii) the heavy chain variable region has the amino acid sequence of SEQ ID NO: 15, and the light chain variable region has the amino acid sequence of SEQ ID NO: 18.

2. A method of treating a disease or disorder selected from the group consisting of osteoporosis, osteopenia, osteoarthritis, and pain associated with osteoarthritis in a human subject in need thereof, comprising administering to said human subject an effective amount of an antibody or antigen-binding portion thereof, that binds human sclerostin and comprises a heavy chain polypeptide that has the amino acid sequence of SEQ ID NO: 3, and a light chain polypeptide that has the amino acid sequence of SEQ ID NO: 6.

* * * * *